US012558253B2

(12) United States Patent  
Holden et al.

(10) Patent No.: US 12,558,253 B2  
(45) Date of Patent: Feb. 24, 2026

(54) OSTOMY POUCH

(71) Applicant: ConvaTec Limited, Flintshire (GB)

(72) Inventors: Clare Holden, Flintshire (GB); Mani Gopal, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 940 days.

(21) Appl. No.: 17/335,476

(22) Filed: Jun. 1, 2021

(65) Prior Publication Data

US 2021/0369484 A1    Dec. 2, 2021

Related U.S. Application Data

(63) Continuation of application No. PCT/GB2021/051338, filed on Jun. 1, 2021.

(30) Foreign Application Priority Data

Jun. 2, 2020    (GB) ..................................... 2008258

(51) Int. Cl.
| | |
|---|---|
| *A61F 5/441* | (2006.01) |
| *A61F 5/44* | (2006.01) |
| *A61F 5/445* | (2006.01) |

(52) U.S. Cl.  
CPC ............ *A61F 5/441* (2013.01); *A61F 5/4404* (2013.01); *A61F 2005/4415* (2013.01); *A61F 5/445* (2013.01)

(58) Field of Classification Search  
CPC . A61F 5/441; A61F 5/4404; A61F 2005/4415  
See application file for complete search history.

(56) References Cited

U.S. PATENT DOCUMENTS 4,411,659 A * 10/1983 Jensen .................... A61F 5/441  
                                                              604/340  
4,723,951 A * 2/1988 Steer ....................... A61F 5/441  
                                                              55/505

(Continued)

FOREIGN PATENT DOCUMENTS

| EP | 3837520 A1 | 6/2021 |
|---|---|---|
| EP | 3454796 B1 | 2/2022 |

(Continued)

OTHER PUBLICATIONS

International Search Report; European Patent Office; International Application No. PCT/GB2021/051338; Sep. 16, 2021; 3 pages.

(Continued)

*Primary Examiner* — Guy K Townsend  
(74) *Attorney, Agent, or Firm* — TAFT STETTINIUS HOLLISTER LLP; Ryan O. White; Derek B. Lavender

(57)                ABSTRACT

The invention relates to an ostomy pouch 10, 110. The pouch 10, 110 comprises an inner wall 18*b*, 118*b* and an outer wall 20*b*, 120*b* sealed about at least part of the periphery thereof to define a cavity for containing a stomal output. An inlet 22, 122 is provided into the cavity for receiving stomal output from an ostomate, in use. The cavity comprises multiple sections 12, 14, 16; 112, 114, 116 separated by waisted sections 13, 15; 113, 115. The maximum width of the sections 12, 14, 16; 112, 114, 116 has a greater width than a minimum width of the waisted section(s) 13, 15; 113, 115.

21 Claims, 6 Drawing Sheets

(56)                References Cited

U.S. PATENT DOCUMENTS

|  |  |  |  |  |
|---|---|---|---|---|
| 5,250,042 | A * | 10/1993 | Torgalkar | A61F 5/441 604/339 |
| 5,690,623 | A * | 11/1997 | Lenz | A61F 5/441 604/332 |
| 5,733,271 | A * | 3/1998 | Bjørn | A61F 5/441 55/482 |
| 6,135,986 | A * | 10/2000 | Leisner | A61F 5/441 604/324 |
| 6,171,288 | B1 * | 1/2001 | Wiltshire | A61F 5/441 604/333 |
| 6,659,988 | B1 * | 12/2003 | Steer | A61F 5/441 604/335 |
| 6,685,684 | B1 * | 2/2004 | Falconer | A61F 5/451 604/355 |
| 6,712,800 | B2 * | 3/2004 | Kanbara | A61F 5/445 604/333 |
| 7,326,190 | B2 * | 2/2008 | Botten | A61F 5/441 604/332 |
| 7,559,922 | B2 * | 7/2009 | Botten | A61F 5/441 604/332 |
| 9,833,352 | B2 * | 12/2017 | Maidl | A61F 5/445 |
| 9,993,363 | B2 * | 6/2018 | Masters | A61F 5/441 |
| 10,285,847 | B2 * | 5/2019 | Lesko | A61F 5/441 |
| 10,478,329 | B2 * | 11/2019 | Oberholtzer | A61F 5/445 |
| 10,478,330 | B2 * | 11/2019 | Wiltshire | A61F 5/445 |
| 11,033,420 | B2 | 6/2021 | Blatt | |
| 11,191,662 | B2 | 12/2021 | Cesa et al. | |
| 11,229,543 | B2 | 1/2022 | Cesa et al. | |
| 11,234,856 | B2 | 2/2022 | Cisko, Jr. et al. | |
| 11,246,739 | B2 | 2/2022 | Ekfeldt et al. | |
| 11,389,319 | B2 | 7/2022 | Botten et al. | |
| 11,491,043 | B2 | 11/2022 | Langhorn et al. | |
| 11,559,425 | B2 * | 1/2023 | Tretheway | A61F 5/445 |
| 11,819,445 | B2 | 11/2023 | Langhorn et al. | |
| 11,957,615 | B2 | 4/2024 | Scalise et al. | |
| 2003/0100870 | A1 * | 5/2003 | Villefrance | A61F 5/441 604/333 |
| 2012/0130329 | A1 * | 5/2012 | March | F16K 3/24 604/332 |
| 2012/0283678 | A1 * | 11/2012 | Nguyen-Demary | A61F 5/445 604/338 |

|  |  |  |  |  |
|---|---|---|---|---|
| 2013/0253455 | A1 * | 9/2013 | Masters | A61F 5/445 604/332 |
| 2020/0276044 | A1 * | 9/2020 | Tretheway | A61F 5/441 |
| 2021/0177642 | A1 | 6/2021 | Andersen et al. | |
| 2021/0244497 | A1 | 8/2021 | Taweh | |
| 2021/0369484 | A1 * | 12/2021 | Holden | A61F 5/4404 |
| 2021/0369485 | A1 * | 12/2021 | Evans | A61F 5/445 |
| 2021/0369486 | A1 * | 12/2021 | Holden | A61F 5/445 |
| 2021/0369491 | A1 * | 12/2021 | Holden | A61F 5/4404 |
| 2021/0369493 | A1 * | 12/2021 | Young | A61F 5/4404 |
| 2021/0369494 | A1 * | 12/2021 | Holden | A61F 5/448 |
| 2022/0096262 | A1 | 3/2022 | Austin | |
| 2022/0110778 | A1 | 4/2022 | Levin | |
| 2022/0168132 | A1 | 6/2022 | Jewell | |
| 2022/0226143 | A1 | 7/2022 | Negrete | |
| 2022/0339022 | A1 | 10/2022 | Weche | |
| 2023/0099447 | A1 * | 3/2023 | Czaplewski | A61F 5/441 604/333 |
| 2023/0218424 | A1 | 7/2023 | Armstrong | |
| 2023/0255814 | A1 | 8/2023 | Donovan et al. | |
| 2023/0355425 | A1 | 11/2023 | Scott | |
| 2024/0082046 | A1 * | 3/2024 | Holden | A61F 5/445 |
| 2024/0207083 | A1 | 6/2024 | Scalise et al. | |

FOREIGN PATENT DOCUMENTS

| EP | 3454797 | B1 | 2/2022 |
|---|---|---|---|
| EP | 3955864 | A1 | 2/2022 |
| EP | 3998052 | A1 | 5/2022 |
| EP | 2942039 | B1 | 7/2022 |
| EP | 3955864 | B1 | 1/2024 |
| EP | 3541332 | B1 | 3/2024 |
| EP | 3451982 | B1 | 4/2024 |
| EP | 3544554 | B1 | 4/2024 |
| EP | 4135637 | B1 | 5/2024 |

OTHER PUBLICATIONS

Written Opinion of the International Searching Authority; European Patent Office; International Application No. PCT/GB2021/051338; Sep. 16, 2021; 6 pages.

* cited by examiner

OSTOMY POUCH

This application is a continuation of International Application No. PCT/GB2021/051338 filed Jun. 1, 2021 and claims the priority of foreign Application No. GB2008258.2 filed Jun. 2, 2020. The disclosures of which are hereby incorporated herein in their entirety.

TECHNICAL FIELD OF THE INVENTION

The present invention relates to an ostomy pouch having a cavity for containing a stomal output.

BACKGROUND TO THE INVENTION

An ostomy pouch may be used to collect and hold stomal output from a stoma formed in the body of an ostomate. Generally the stoma is a surgical opening in the torso of the ostomate's body, but may also refer to internal tissue, organs or portions thereof that are exposed by the opening. Ostomy pouches typically take the form of a pair of walls sealed together to form a cavity into which stomal output may be expelled from the ostomate through a formed stoma.

One exemplary prior art urostomy pouch is disclosed in GB2268882. The pouch comprises front and rear walls joined by a peripheral weld, and includes an additional pair of V-shaped welds extending inwardly to define a non-return valve. The V-shaped welds could be seen as defining a single waist between a first (upper) and a second (lower) section of the pouch.

Another exemplary urostomy pouch is disclosed in EP1068848. The pouch consists substantially of a first upper curved arcuate portion and a second lower arcuate portion, at least one of the arcuate portions having a maximum width greater than the width at the "waist", where the two portions meet. The disclosure describes this arrangement as being "figure of 8" shaped, but it is notable that the upper section of the "8-shape", is no wider than the "slight waist".

Given the nature and use of ostomy pouches, it is desirable for a pouch to be able to be worn by an ostomate as easily and discreetly as possible. It is also advantageous for the pouch to be worn for an extended period of time for increased convenience for the ostomate. However, in order to increase the length of time a pouch can be used it is typically necessary to increase the volume of the pouch, which may be detrimental in terms of the discreetness of the pouch, in use. Some ostomy pouches may be provided with a drain allowing the ostomate to drain stomal output from the cavity. This may give the ostomate added control over the amount of output within the cavity at any one time, but at the cost of reduced convenience where the ostomate is required to intermittently drain the pouch.

It would therefore be advantageous to provide an ostomy pouch with increased capacity but which does not suffer the same drawbacks of the prior art in terms of reduced discreetness for the ostomate.

It is an aim of an embodiment or embodiments of the invention to overcome or at least partially mitigate one or more problems with the prior art.

SUMMARY OF THE INVENTION

According to an aspect of the invention there is provided an ostomy pouch, comprising: a cavity for containing a stomal output, the cavity including, at least: a first section, second section and a third section, a first waisted section located between the first section and second section; and a second waisted section located between the second and third section.

According to an aspect of the invention there is provided an ostomy pouch, comprising: an inner wall and an outer wall sealed about at least part of the periphery thereof to define a cavity for containing a stomal output, the cavity including, at least: a first section, a second section and a third section; a first waisted section located between the first section and second section; and a second waisted section located between the second section and the third section; wherein the first and second sections have a maximum width greater than a minimum width of the first waisted section; and wherein the second and third sections have a maximum width greater than a minimum width of the second waisted section.

Advantageously, the ostomy pouch of the present invention may permit an ostomate to increase the period of use of the pouch compared to prior art appliances. This is achieved by providing an increased cavity volume for the pouch while maintaining ostomate discretion and comfort. Further, the provision of a pair of waisted sections may control (i.e. prevent or substantially reduce) sagging of the pouch when filled with stomal output, allowing for a greater volume of stomal output to be contained within the pouch before an ostomate feels it necessary to empty or replace the pouch. This may be particularly beneficial for use in instances where there is a high stomal output. In some instances this is further benefitted by providing means for draining the cavity of stomal output reliably and hygienically so as to increase an ostomate's confidence in reusing the pouch compared to some prior art appliances. Since the ostomate may be inclined to use each ostomy appliance of the present disclosure for longer, the total number of ostomy appliances used by the ostomate in a given time period may be reduced. This may produce an environmental benefit in reducing the amount of environmental waste produced.

Optional features set out below may apply to any aspect of the invention as appropriate.

The ostomy pouch may be configured to be used in a substantially vertical orientation. In such embodiments, the first section may form an upper section of the pouch. The third section may form a lower section of the pouch. The second section may form an intermediate section between the upper and lower sections.

The ostomy pouch may be configured to be used in a substantially horizontal orientation. In such embodiments, the first section may form a first end section. The third section may form a second end section. The second section may form an intermediate section between the first and second end sections. In embodiments, the first section forms a right-side section of the pouch. The third section may form a left-side section of the pouch. The second section may form an intermediate section between the right and left side sections.

The inner wall of the pouch may comprise an inlet for receiving the stomal output into the cavity. The inlet may be provided within a portion of the inner wall defining at least part of the first section of the cavity. In presently preferred embodiments, the inlet is provided within a portion of the inner wall defining at least part of an upper section of the pouch. In further embodiments, the inlet may be provided within a portion of the inner wall defining at least part of the second section, and preferably an intermediate section of the pouch, for example when used in a substantially horizontal orientation.

The pouch may comprise a closed pouch. In alternative embodiments, the pouch may comprise an open pouch, and comprise a drain for releasing stomal output from the cavity. The drain may comprise a drain aperture comprising an opening within the pouch for releasing stomal output from the cavity. The drain and/or drain aperture may be defined, at least in part, by the inner and outer walls of the pouch.

The drain may comprise a deployable drain, which may be moveable between a stowed position and a deployed position. The deployable drain may be moveable between stowed and deployed positions by rolling or folding the drain, e.g. about one or more fold lines in the drain.

The pouch may comprise a fastening arrangement for retaining the drain in a stowed position. The fastening arrangement may comprise one or more fasteners. The one or more fasteners may comprise a pair of fastening elements. The fastening elements may comprise a strip of hook fasteners and a strip of loop fasteners together forming a hook and loop fastener arrangement. The fastening elements may comprise two strips of hook fasteners forming a dual hook fastener arrangement. The pouch may comprise a first fastening element located on the inner wall of the pouch. The second fastening element may be provided on the outer wall of the pouch, or in some embodiments on an outer comfort layer of the pouch. The second fastening element may be provided on a flap, which itself may be secured (e.g. adhesively or otherwise) to the outer wall or outer comfort layer (where present) of the pouch.

The drain may comprise one or more pursing strips. The pursing strip(s) may be associated with the inner or outer wall of the pouch. For example, the pursing strips may be adhesively or otherwise fixed to the inner or outer wall of the pouch. The pursing strip(s) may assist in separating the inner and outer walls of the pouch, in a portion thereof, to define a drain aperture in the pouch for draining stomal output from the cavity.

In embodiments, the drain is provided in the third section of the pouch. In preferred embodiments, the drain is provided in a lower section of the pouch, e.g. where the pouch is configured to be used in a substantially vertical orientation.

The pouch may comprise a filter arrangement. The filter arrangement may comprise a vent for venting of gaseous stomal output from the cavity. The filter arrangement may comprise an odour filter. The odour filter may comprise a charcoal or activated carbon filter, for example. The odour filter may be substantially circular or disc shaped. A major face of the circular/disc shaped filter may be open allowing for gaseous stomal output to enter the filter therethrough. The odour filter may comprise a strip filter which may have open ends, for example.

The filter arrangement, or components thereof—e.g. the vent—may be provided within or be associated with the outer wall of the ostomy pouch. For example, in some embodiments, the filter arrangement may comprise an odour filter positioned on an exterior surface of the outer wall of the pouch. In such embodiments, the vent may comprise an opening within the outer wall, e.g. a substantially circular opening, positioned proximal to the odour filter and providing a vent through which gaseous stomal output may exit the interior of the pouch and enter the odour filter, in use. Advantageously, having the odour filter exterior to the interior of the pouch may minimise exposure of the filter to stomal output, particularly solid and liquid stomal output which may clog the filter if exposed for an extended period of time, and in doing so may result the pouch to undesirably bloat or balloon. Such an arrangement may be particularly useful for open pouches, for example, where the same pouch may be used for a prolonged period by a user.

In other embodiments the filter arrangement may comprise an odour filter provided on an interior surface of the outer wall of the pouch. In such embodiments, the vent may comprise one or more slits, openings or the like within the outer wall of the ostomy pouch. The slits may be positioned adjacent to the odour filter, for example adjacent to a rear face of the odour filter which is adhered or otherwise coupled to the outer all of the pouch. Whilst suffering the drawbacks of the potential of having the liquid and solid stomal output in contact with the odour filter for extended periods, embodiments wherein the odour filter is provided within the interior of the pouch may provide a cost-effective solution, and may be particularly suited for use with closed pouches, for instance, which are designed for wear for a much shorter period of time when compared with open pouches. Here, the filter may be exposed to the stomal output, but for a much shorter period of time and therefore may be less likely to clog before the end of its use period.

The filter arrangement may comprise a pre-filter. The pre-filter may be configured to control the content of stomal output in contact with the vent and/or odour filter. For example, the pre-filter may be advantageously configured to prevent or at least reduce the level of solid or liquid stomal output able to come into contact with the vent and/or odour filter.

The filter arrangement may be provided within or be associated with the outer wall of the ostomy pouch. For example, the vent may comprise one or more slits, openings or the like within the outer wall of the ostomy pouch. The filter arrangement may be provided within, or be associated with the first section of the pouch, and preferably an upper section of a pouch configured to be used in a substantially vertical orientation.

The filter arrangement may be provided with a filter cap. The filter cap may be provided on an exterior surface of the outer wall of the pouch, or an exterior surface of an outer comfort layer, where present, for example, and may be positioned about an odour filter forming part of the filter arrangement of the pouch. The filter cap may provide protection for the filter arrangement, and in particular may be provided about and be operable to protect an odour filter, in use. The filter cap may include one or more openings or slits therein, e.g. one or more s-slits, which allow for the venting of gas therethrough.

The filter arrangement may additionally include a filter cover label. The filter cover label may comprise a removeable component which may be positioned over the filter cap, in use, to seal the openings/slits therein. This may be particularly useful, for example, where an ostomate plans to swim, bathe or shower. The label may prevent ingress of water through said openings/slits in the cap and thereby prevent clogging of the odour filter from water.

The maximum widths of the first, second and/or third sections may be equal (or substantially equal). The maximum width of the first, second and/or third sections may be different. For example, in some embodiments the maximum width of the first section may be greater than the maximum width of the second and/or third sections. The maximum width of the second section may be greater than the maximum width of the first and/or third sections. The maximum width of the third section may be greater than the maximum width of the first and/or second sections. In presently preferred embodiments, the maximum width of the first section is greater than the maximum width of the second section, and the maximum width of the second section is greater than the maximum width of the third section. In further embodiments, the maximum width of the first and third sections may be greater than the maximum width of the second section. For example, the maximum width of the first and third sections may be approximately equal, and greater than the maximum width of the second section.

The maximum width of the first, second and/or third section may be between 120 mm to 170 mm, or between 130 mm to 160 mm, or between 135 mm to 150 mm, or between 135-140 mm, or between 140 mm to 145 mm, for example. In an exemplary embodiment, the maximum width of the first section may be between 140 mm to 142 mm, the maximum width of the second section may be between 137 mm to 139 mm, and the maximum width of the third section may be between 134 mm to 136 mm.

The minimum width of the first and/or second waisted sections may be between 105 mm to 135 mm, or between 110 mm to 130 mm, or between 110 mm to 125 mm, or between 115 mm to 130 mm, or between 120 mm to 135 mm, or between 115 mm to 120 mm, or between 120 mm to 125 mm, or between 125 mm to 130 mm, or approximately 120 mm, for example. In an exemplary embodiment, the minimum width of the first and/or second waisted sections may be approximately 129 mm, or 119 mm, or 109 mm.

The minimum width of the first waisted section may be between 5 mm to 30 mm less than the maximum width of the second section, or between 10 mm to 20 mm less than the maximum width of the second section, or between 15 mm to 20 mm less than the maximum width of the second section. The minimum width of the waisted section may be between 10 mm to 35 mm less than the maximum width of the first section, or between 15 mm to 30 mm less than the maximum width of the first section, or between 20 mm to 25 mm less than the maximum width first section, for example.

The minimum width of the first waisted section may be between 75% to 95% of the maximum width of the second section, or between 80% to 90% of the maximum width of the second section, or between 83% to 88% of the maximum width of the second section. The minimum width of the first waisted section may be between 73% to 92% of the maximum width of the first section, or between 75% to 85% of the maximum width of the first section, or between 80% to 85% of the maximum width of the first section.

The minimum width of the second waisted section may be between 5 mm to 30 mm less than the maximum width of the third section, or between 10 mm to 20 mm less than the maximum width of the third section, or between 15 mm to 20 mm less than the maximum width of the third section. The minimum width of the waisted section may be between 10 mm to 35 mm less than the maximum width of the second section, or between 15 mm to 30 mm less than the maximum width of the second section, or between 20 mm to 25 mm less than the maximum width second section, for example.

The minimum width of the second waisted section may be between 75% to 95% of the maximum width of the third section, or between 80% to 90% of the maximum width of the third section, or between 83% to 88% of the maximum width of the third section. The minimum width of the second waisted section may be between 73% to 92% of the maximum width of the second section, or between 75% to 85% of the maximum width of the second section, or between 80% to 85% of the maximum width of the second section.

In embodiments wherein the pouch is a closed pouch, the pouch may have a length of between 150 mm to 350 mm, or between 200 mm to 300 mm, or between 200 mm to 250 mm, or between 205 mm to 235 mm, or between 208 mm to 230 mm, for example. In embodiments wherein the pouch is an open pouch, the pouch may have a length of between 200 mm to 400 mm, or between 225 mm to 350 mm, or between 250 mm to 300 mm, or between 260 mm to 290 mm, or between 270 mm to 280 mm, for example. In embodiments wherein the pouch comprises a deployable drain, the pouch may have a length of between 240 mm to 350 mm when the deployable drain is in a deployed position, and a length of between 200 mm to 240 mm with the deployable drain in a stowed position.

Opposing edges of the first and/or second waisted sections may each be concavely-curved. Opposing edges of the first and/or second waisted sections may each have a radius of curvature, or a blend of radii of curvature, wherein the or each radii of curvature may be between 20 mm to 60 mm, or between 30 mm to 50 mm, or between 35 mm to 45 mm, for example. The or each radii of curvature may be approximately 40 mm. Opposing edges of the first and/or second waisted sections may be configured in substantially the same way or form, and may be mirror images of each other, for example.

The first, second and or third sections may be generally rounded in shape. For example, the first section may comprise a continuously curved edge that extends from a first edge (e.g. a left-hand edge) of the first waisted section to a second edge (e.g. a right-hand edge) of the second waisted section. The second section may comprise a first continuously curved edge that extends from a first edge (e.g. a left-hand edge) of the second waisted section to a first edge (e.g. a left-hand edge) of the first waisted section. The second section may comprise a second continuously curved edge that extends from a second edge (e.g. a right-hand edge) of the second waisted section to a second edge (e.g. a right-hand edge) of the first waisted section. The third section may comprise a continuously curved edge that extends from a first edge (e.g. a left-hand edge) of the second waisted section to a second edge (e.g. a right-hand edge) of the second waisted section.

The continuously curved edge of the first, second and/or third sections may be convexly curved. The continuously curved edge of the first, second and/or third sections may be absent any points of inflection or abrupt changes in contour. The continuously curved edge of the first, second and/or third sections may have a radius of curvature, or a blend of radii of curvature, wherein the or each radii of curvature may be between 40 mm to 80 mm, or between 55 mm to 75 mm, or between 60 mm to 73 mm, or between 65 mm to 70 mm, for example. The or each radii of curvature for the first, second and third sections may be substantially equal. In embodiments, the or each radii of curvature for the second section may be greater than the or each radii of curvature for the first and/or third sections.

In other embodiments one or more of the first, second and/or third sections may comprise one or more edges which are substantially straight. For example, the second section may comprise a first substantially straight edge that extends from a first edge (e.g. a left-hand edge) of the first waisted section to a first edge (e.g. a left-hand edge) of the second waisted section. The second section may comprise a second substantially straight edge that extends from a second edge (e.g. a right-hand edge) of the first waisted section to a second edge (e.g. a right-hand edge) of the second waisted section. In such embodiments the first and/or third sections may be generally rounded in shape in the manner described hereinabove.

A junction between the first or second sections and the first waisted section may be demarcated by a single point of inflection between a left-hand edge of the first or second section and a left-hand edge of the first waisted section, and by a single point of inflection between a right-hand edge of the first or second section and a right-hand edge of the first waisted section. A junction between the second or third sections and the second waisted section may be demarcated by a single point of inflection between a left-hand edge of the second or third section and a left-hand edge of the second waisted section, and by a single point of inflection between a right-hand edge of the second or third section and a right-hand edge of the second waisted section.

A location of the minimum width of the first waisted section may be at a distance of between 90 mm to 125 mm, or between 95 mm to 120 mm, or between 100 mm to 115 mm, or between 105 mm to 115 mm, or approximately 99 m, 109 mm, 119 mm from an uppermost edge of the ostomy pouch. A location of the minimum width of the second waisted section may be at a distance of between 90 mm to 125 mm, or between 95 mm to 120 mm, or between 100 mm to 115 mm from a lowermost edge of the ostomy pouch. The distance between the location of minimum width of the first waisted section and the uppermost edge of the ostomy pouch, and/or the distance between the location of minimum width of the second waisted section and the lowermost edge of the ostomy pouch may be between 20% to 45% of the length of the pouch, or between 25% to 40% of the length of the ostomy pouch, or between 30% to 35% of the length of the ostomy pouch, for example.

The inner wall and the outer wall may be joined together by a single continuous edge seal. For example, where the pouch comprises a closed pouch, the single continuous edge seal may form a closed peripheral seal. Where the ostomy pouch comprises an open pouch, the single continuous edge seal may extend from a first edge (e.g. a left-hand edge) of a drain aperture to a second edge (e.g. a right-hand edge) of a drain aperture of the pouch. The single continuous edge seal may comprise a weld, which may optionally have a width of between 2 mm to 6 mm, or between 3 mm to 5 mm, or approximately 4 mm, for example. The single continuous edge seal may have a constant width around the periphery of the ostomy pouch.

The inner wall and the outer wall may be formed from flexible sheet material. The flexible sheet material may comprise a single layer or a laminate of a plurality of layers. The flexible sheet material of the inner wall and/or the outer wall may comprise polyvinylidene chloride (PVDC) and/or ethylene-vinyl acetate (EVA). The inner wall and/or the outer wall may have a thickness of between 50 to 150 micrometres, or between 75 to 125 micrometres, or between 75 to 100 micrometres, for example.

The pouch may further comprise at least one comfort layer overlying at least a portion of one of the inner wall and outer wall. The pouch may comprise an inner comfort layer and/or an outer comfort layer.

Where present, the outer comfort layer may comprise a first part and a second part which may be joined to the outer wall so that the first part partially overlaps the second part in an overlap region. The first part and the second part may be separable from each other in the overlap region to form a window opening for viewing the cavity. The overlap region may be angled to extend horizontally when the pouch is in use. The first part and the second part of the outer comfort layer may be configured to slide over each other in the overlap region to accommodate expansion of the underlying outer wall. The first part and the second part may be joined to each other at a first end and at a second end of the overlap region. The first part and the second part may be welded to each other at the first end and at the second end of the overlap region, optionally as part of a peripheral weld of the pouch. External edges of the one or more parts of the outer comfort layer are shaped and sized to correspond to the shape, form and contours of the outer wall.

Where present, the inner comfort layer may comprise a single part or multiple parts. The inner comfort layer may cover only a portion of the inner wall. However, preferably the inner comfort layer covers substantially the whole of the inner wall. An aperture may be provided in the inner comfort layer corresponding to the location of the inlet in the inner wall of the pouch. The inner comfort layer may be shaped and sized to correspond to the shape, form and contours of the inner wall. The inner comfort layer may be provided with a wafer aperture that corresponds to the location of the inlet of the inner wall to permit fluid connection of the inlet of the inner wall to an ostomy wafer.

The at least one comfort layer may be formed from a flexible sheet material. The material of the flexible sheet material may comprise one or more of polyester, nylon, viscose, polyurethane, polyethylene, polypropylene, polyvinylidene chloride (PVDC) and ethylene-vinyl acetate (EVA). The at least one comfort layer may comprise a laminate of two or more layers. The at least one comfort layer may comprise at least one fabric layer and at least one film layer. The at least one film layer may be laminated to the at least one fabric layer, and optionally may be laminated to the at least one fabric layer over an entire area of the at least one comfort layer. The at least one fabric layer may comprise a woven or a non-woven textile layer. The fabric layer may comprise polyester, nylon, viscose, polyethylene or polypropylene. The at least one film layer may comprise polyurethane, polyvinylidene chloride (PVDC) or ethylene-vinyl acetate (EVA). The at least one comfort layer may have a thickness of between 50 to 1000 micrometres, or between 60 to 500 micrometres, or between 75 to 300 micrometres, or between 100 to 200 micrometres, for example.

The inner wall and the inner comfort layer may be joined together around their peripheral edges and/or the outer wall and the outer comfort layer may be joined together around their peripheral edges. The joining may be by use of welding, adhesive or equivalent means. A single joining operation may be used to join the inner comfort layer, the inner wall, the outer wall and the outer comfort layer together. For example a single weld may be used to join the four layers.

The cavity may be a single volume or may be sub-divided into two or more chambers. For example, the two or more chambers may be separated by one or more partitions, wall members, or filter elements, for example. In some embodiments the pouch comprises a separation wall between the inner and outer walls defining the cavity into first and second chambers. The separation wall may comprise a filtering element. The filtering element may be fluid-permeable, and may be operable to filter fluid stomal output from solid stomal output.

The filtering element may include an array of apertures allowing the passage of fluid stomal output therethrough. The apertures may have a diameter of between 0.02 mm to 0.10 mm, or between 0.03 mm to 0.08 mm, or between 0.04 mm to 0.06 mm, or between 0.06 mm to 0.08 mm, or between 0.10 mm to 0.40 mm, for example. The spacing between adjacent apertures in the array may be between 0.80 mm to 2.20 mm, or between 1.00 mm to 2.00 mm, or between 1.25 mm to 1.75 mm, for example. The apertures may extend across at least 50%, or at least 75%, or at least 80%, or at least 90% of the surface of the filtering element. The filtering element may extend across at least the lower half or lower quarter of the cavity, and/or may extend across at least the upper half or upper quarter of the cavity.

In use, the first chamber of the cavity is arranged to receive both fluid and solid stomal output from the ostomate via the inlet in the inner wall. The separation wall is arranged to allow passage of fluid stomal output into the second chamber, retaining the solid stomal output in the first chamber. In embodiments wherein the pouch comprises a filter arrangement, the filter arrangement may further be used to separate gaseous stomal output from fluid stomal output, allowing the gaseous stomal output to be removed from the cavity.

The pouch may comprise either an ostomy wafer that is located within or otherwise associated with the inlet of the inner wall, or a releasable coupling that is located within or is otherwise associated with the inlet of the inner wall. In embodiments, the releasable coupling may be configured for coupling with a body fitment component comprising an ostomy wafer. Where present, the ostomy wafer may extend through an aperture of the inner wall and/or inner comfort layer. The ostomy wafer may be provided with a releasable liner which may be removed by a user prior to securing the pouch to the ostomate, in use.

The pouch may comprise only three sections. Alternatively, the pouch comprises at least three sections. The pouch may comprise one or more further sections, for example a fourth section, and/or a fifth section. The one or more further sections may be separated from one or more other sections of the pouch by respective waisted sections. The waisted sections may have a minimum width which is less than the maximum width of the further section(s).

According to an aspect of the invention there is provided a method for collecting stomal output using an ostomy pouch according to any aspect described herein. The method may comprise attaching the ostomy pouch about a stoma of an ostomate. The ostomy pouch may be attached about the stoma through use of an ostomy wafer of the pouch where the pouch comprises a one-piece ostomy pouch. Alternatively, the method may comprise attaching an ostomy wafer of a body fitment component of a two-piece ostomy pouch about the stoma; and attaching a pouch to the body fitment component. The pouch may be attached to the body fitment component before or after the ostomy wafer has been attached about the stoma. Where the ostomy pouch comprises an open or drainable pouch, the method may comprise draining stomal output from the ostomy pouch.

DETAILED DESCRIPTION OF THE INVENTION

In order that the invention may be more clearly understood one or more embodiments thereof will now be described, by way of example only, with reference to the accompanying drawings, of which:

When used herein and throughout the specification, the term "stomal output" refers to any gases, liquids or solids produced by an ostomate that may be secreted from a stoma or that exit a stoma of the ostomate. The stomal output may comprise gaseous, fluid, liquid and/or solid stomal output.

The term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

The term "ostomate" refers to a subject that may have use of the ostomy pouch described herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

Ostomy pouches disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, a ureterostomy, or a vesicostomy. The ostomy pouches disclosed herein may be used with additional devices including, but not limited to, a shunt, a catheter, a plug or a faecal management system.

In this specification locations and orientations of features may be described with reference to the ostomy pouch being "in use", "orientated as it would be in use" or similar. Such terms refer to the intended orientation of the ostomy pouch when it is adhered or otherwise secured to a body of an ostomate, e.g. with the ostomate in a standing position, irrespective of whether the ostomy pouch is currently performing such a use or the actual position of the ostomate. The terms "upper" and "lower" and related terms refer to the relative position of a part or portion of the ostomy pouch when orientated as it may be in use. For example, a section of the ostomy pouch may be referred to as an "upper" section of the ostomy pouch. In such an example, said section will be intended to be the uppermost section (in the vertical direction) of the ostomy pouch when attached to the body of a standing ostomate. However the reader skilled in the art will appreciate that before attachment to the ostomate said section may not always be the uppermost section and in addition when attached the section may not always be the uppermost section if the ostomate adopts a non-standing position, for example lying down.

Figure 1B:
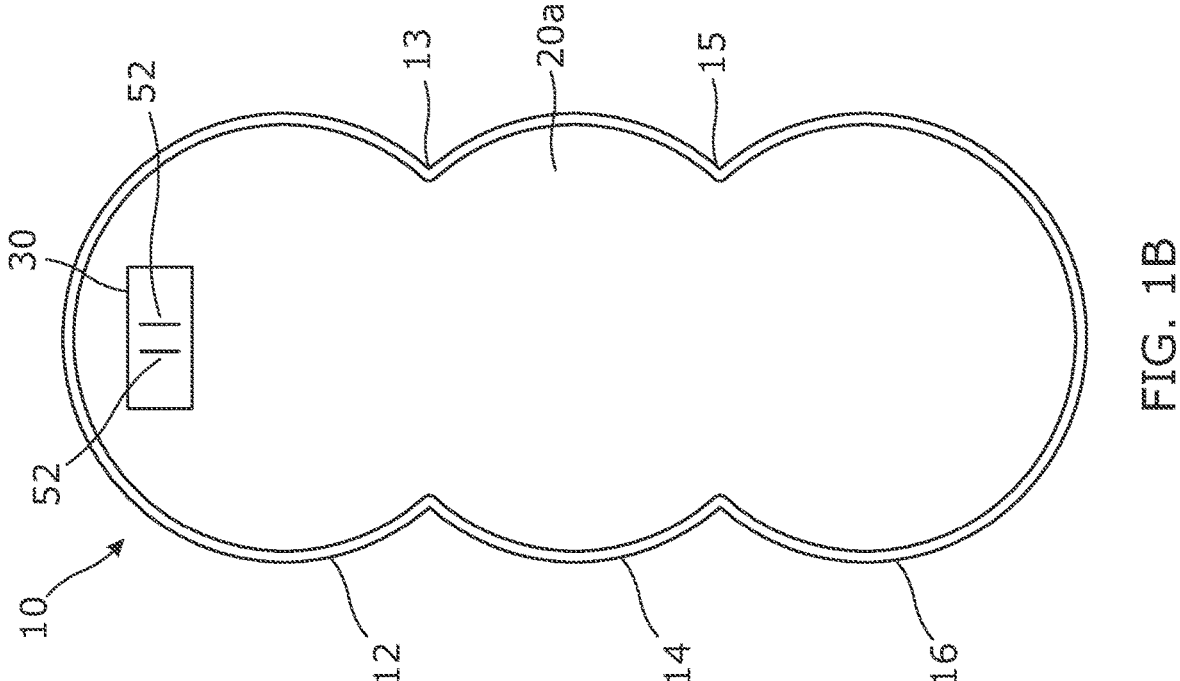
FIG. 1B is a further side perspective view of the ostomy pouch shown in FIG. 1A.
Figure 1A:
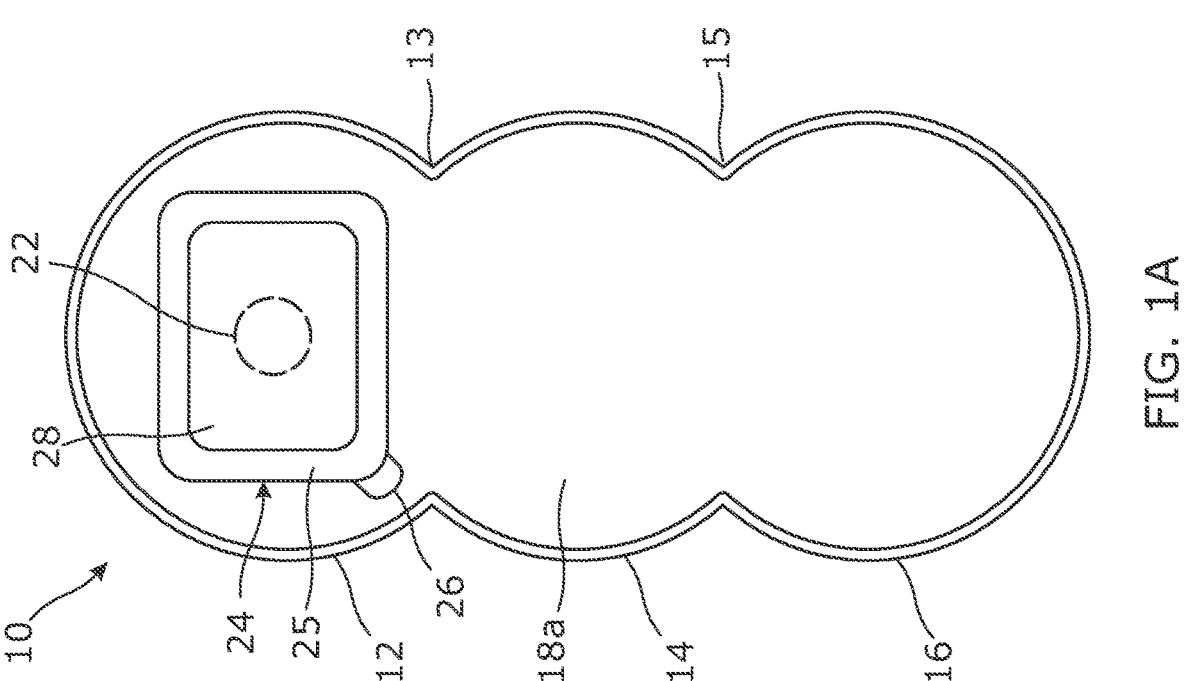
FIG. 1A is side perspective view of a first embodiment of an ostomy pouch of the invention.

The terms "left-hand" and "right-hand" and related terms may refer to the ostomy pouch when viewed from the rear (for example, as shown in FIG. 1A). Thus, as an illustrative example, a "left-hand" edge of the ostomy appliance will be towards a left-hand side of the ostomate in the situation where the ostomy pouch is attached to the front torso of the ostomate.

The terms "concave" and "convex" and related terms refer to shaping of features of the ostomy pouch when viewed from an exterior of the ostomy pouch. Thus, as an illustrative example, an ostomy wafer of circular shape would be considered to have a convexly shaped peripheral edge.

The terms "inner" and "outer" refer to the relative position of a part or portion of the ostomy pouch with reference to the body of an ostomate when the ostomy pouch is attached (e.g. adhesively or otherwise) to the body of the ostomate. "Inner" refers to a position relatively closer to the body of the ostomate than a comparative position that is "outer". "Outer" refers to a position relatively further away from the body of the ostomate than a comparative position that is "inner".

Ostomy pouches are commonly attached to the body of an ostomate by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." The "ostomy wafer", "adapter," "wafer," "baseplate", or "layered adhesive wafer" may form a skin barrier between the ostomate and the pouch. In this specification, the term "ostomy wafer" includes ostomy wafers for a "two-piece appliance" and for a "one-piece appliance".

A "two-piece pouch" refers to an ostomy pouch where the ostomy wafer forms part of a separate body fitment component that is attached by a releasable coupling to a pouch. A two-piece pouch permits the body fitment component to be separated from the pouch without damage, so that at least one of the parts continues to be functionally usable. For example, the body fitment component may remain in place on the body of the ostomate. In contrast, a "one-piece pouch" refers to an ostomy pouch where the ostomy wafer is permanently attached to the appliance, to the extent that the ostomy wafer cannot easily be separated without risk of damaging the appliance. A one-piece pouch is intended to be used as an integral unit.

Ostomy pouches may commonly be configured as "closed" pouches or "open" pouches. In this specification a "closed pouch" refers to an ostomy pouch where it is not intended that stomal output is drained from the cavity. Thus, a closed pouch may typically be configured as a one-use, disposable and non-reusable pouch. In this specification an "open pouch" refers to an ostomy pouch where it is possible for the stomal output to be drained from the cavity and the pouch reused. Thus, an open pouch may be configured as a reusable pouch, such that it can be reused and emptied multiple times whilst attached to the body, although this is not essential. In an open pouch the stomal output may be drained intermittently as instigated by an action of the ostomate or may be drained intermittently or continuously due to the cavity being fluidly connected to a drain, for example a night drain line.

The use of a closed pouch or an open pouch may be, in part, due to user preference, but equally either a closed or open pouch may be more suited depending on the particular ostomate's needs, and depending on the position of the stoma for the ostomate. For example, for stomas formed via ileostomy the stomal output may tend to be looser and be easily drainable which may lead to an open pouch being suitable. For stomas formed by colostomy, the stomal output may tend to be more solid and may not be readily drained by a user. In such instances, a closed pouch may be more suited.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The Figures illustrate a series of embodiments of the invention. Where equivalent components are present between embodiments, like reference numerals have been used.

In general, the present invention relates to an ostomy pouch 10, 110, having an inner wall 18*b*, 118*b* and an outer wall 20*b*, 120*b* sealed about at least part of the periphery thereof to define a cavity for containing a stomal output.

Figure 1C:
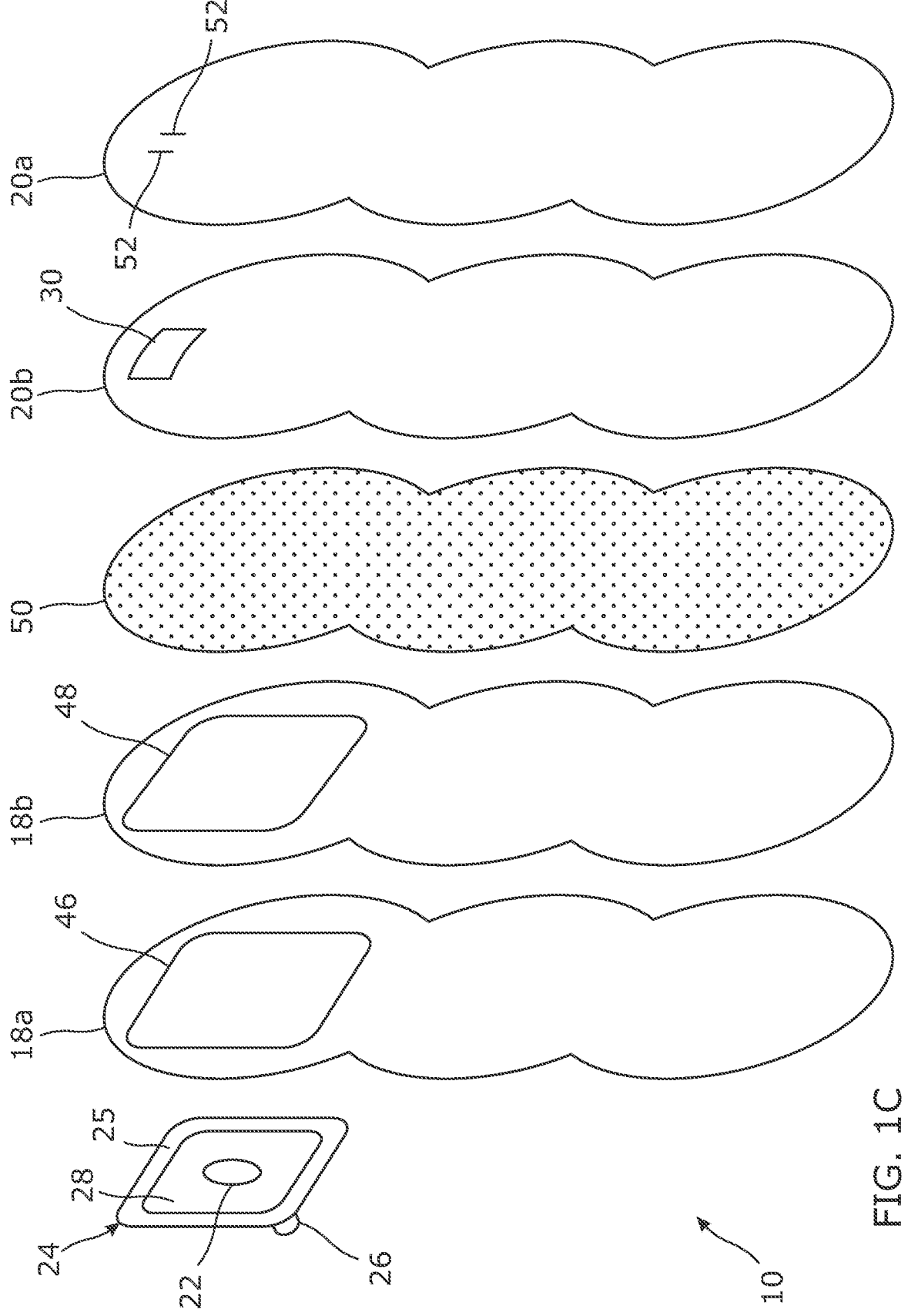
FIG. 1C is an exploded perspective view of the ostomy pouch shown in the preceding Figures.
Figure 2B:
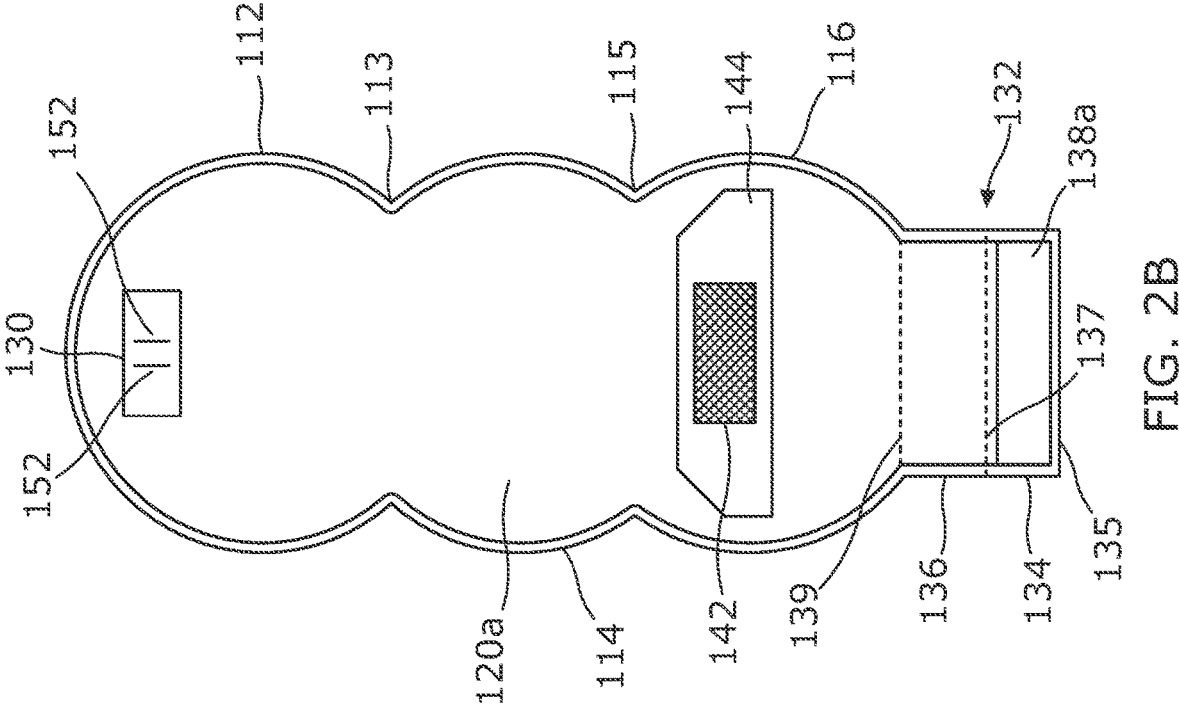
FIG. 2B is a further side perspective view of the ostomy pouch shown in FIG. 2A.
Figure 2A:
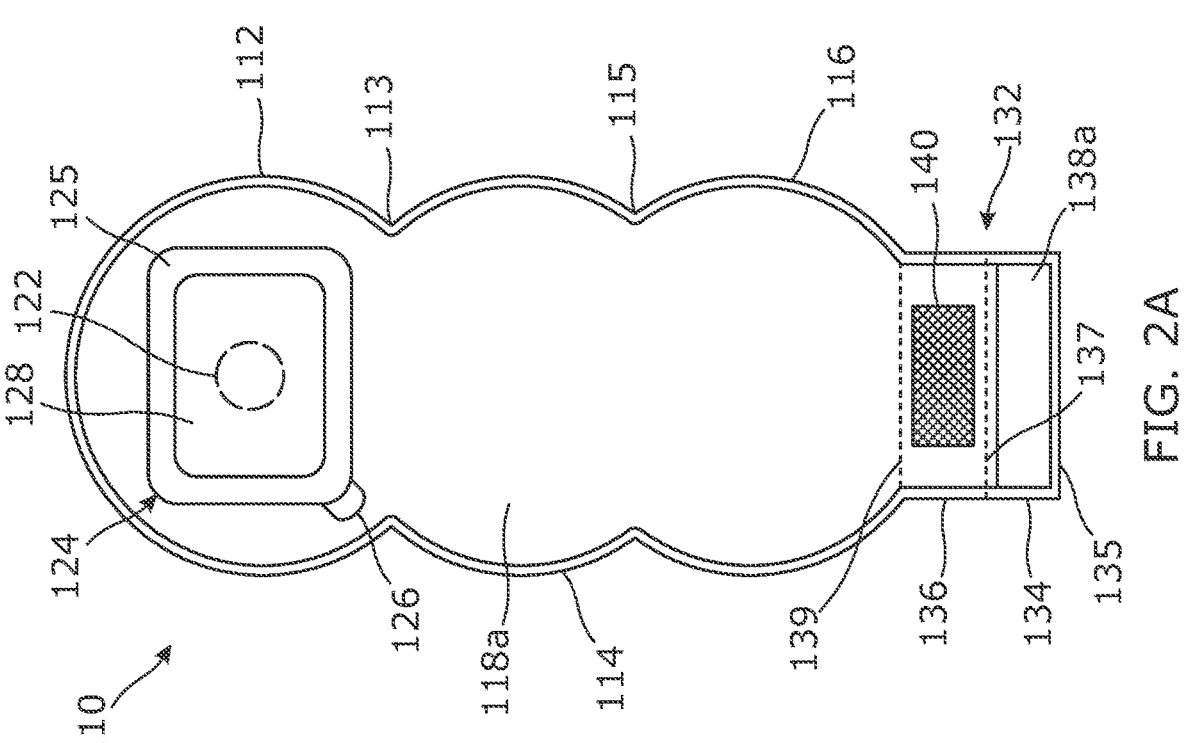
FIG. 2A is a side perspective view of a second embodiment of an ostomy pouch of the invention.

FIGS. 1A-1C illustrate a first embodiment of an ostomy pouch 10 of the present invention.

The pouch 10 comprises an inner wall 18*b* and an outer wall 20*b* which are sealed about their periphery and define a cavity for containing a stomal output. The pouch 10 is a closed pouch, with the seal provided as a single, continuous seal about the entire perimeter of the pouch 10. The cavity includes a first section 12, a second section 14 and a third section 16 which are generally rounded in shape with convex curved edges, defining an upper section 12, lower section 16 and intermediate section 14 positioned between the upper and lower sections 12, 16. The upper, intermediate and lower sections 12, 14, 16 are separated by waisted sections 13, 15 which are narrower in width than upper, intermediate and lower sections 12, 14, 16. Specifically, the pouch 10 includes a first waisted section 13 which is located between the upper section 12 and intermediate section 14, with the maximum width of the upper section 12 and intermediate section 14 being greater than the minimum width of the first waisted section 13. Further, the pouch 10 includes a second waisted section 15 which is located between the intermediate section 14 and lower section 16, with the maximum width of the intermediate section 14 and lower section 16 being greater than the minimum width of the second waisted section 15.

The inner and outer walls 18*b*, 20*b* are formed of a flexible, plastics sheet material. The pouch 10 also includes inner and outer comfort layers 18*a*, 20*a* which overlie respective inner and outer walls 18*b*, 20*b*. The comfort layers 18*a*, 20*a* are formed of a woven, fabric material and define an outer surface of the pouch 10. In the illustrated embodiment, a single joining operation is used to join the inner comfort layer 18*a*, the inner wall 18*b*, the outer wall 20*b* and the outer comfort layer 20*a* together, here through welding.

The inner wall 18*b* comprises an opening therein defining a stomal inlet 48 in the pouch 10 for receiving stomal output into the cavity. Here, the stomal inlet 48 is provided within the upper section 12 of the pouch 10. An aperture 46 is provided in the inner comfort layer 18a defining a wafer aperture into which an ostomy wafer 24 is located and positioned over the stomal inlet 48, in use.

The ostomy wafer 24 includes a central aperture 22, an adhesive region 28, and a removable release liner 25 for exposing the adhesive region 28 which may subsequently be used to secure the pouch 10 to and about the stoma of the ostomate, in use. A tab 26 is provided on the release liner 25 to assist the user in removing the release liner 25. The ostomy wafer 24 is suitably secured to the inner wall 18b, e.g. through use of a further adhesive region. The adhesive region 28 is mouldable to the extent that it may be manipulated to adjust the shape and size the central aperture 22 according to the size and shape of the ostomate's stoma. When used here and throughout the specification, the term "mouldable" is intended to cover a component, here the adhesive region 28, which can be shaped under application of a force (e.g. rolling) by a user. In an alternative arrangement the adhesive region may be configured such that it may be shaped to fit the stoma by a user cutting the region to make the central aperture 22 the required size and shape, for example.

A separation filter 50 is provided within the pouch 10, positioned between the inner and outer walls 18b, 20b, separating the cavity into two chambers. The separation filter 50 is fluid-permeable, and is operable to filter fluid (i.e. gaseous and liquid) stomal output from solid stomal output. Specifically, and in use, stomal output is received through the stomal inlet 48 into the first chamber of the cavity. This stomal outlet may be both fluid and solid. The separation 50 is arranged to allow passage of fluid stomal output into the second chamber, proximal to the outer wall 20b, whilst retaining the solid stomal output in the first chamber, proximal to the inner wall 18b. In the illustrated embodiment, the separation filter 50 is shaped and sized substantially the same as the inner and outer walls 18b, 20b, and is sealed about its periphery to the inner and outer walls 18b, 20b.

A further filter arrangement 30 is provided in the outer wall 20b for venting of gaseous stomal output from the cavity. This can advantageously maximise the capacity of the pouch 10 for receiving liquid and solid stomal output, and prevent "bloating" or "ballooning" of the pouch 10 which may adversely affect discreetness of the pouch 10 in use. The filter arrangement 30 is provided within the upper section 12 of the pouch.

The filter arrangement 30 includes a vent and an odour filter (e.g. a charcoal or activated carbon filter) for reducing the release of unpleasant odours from the cavity. Slits 52 are provided in the outer comfort layer 20a proximal to the position of the filter arrangement 30 such that gaseous stomal output release through the filter arrangement 30 is released from the pouch 10. The separation filter 50 advantageously prevents solid stomal output from coming into contact with the filter arrangement 30, thereby preventing or reducing the likelihood of the filter arrangement 30 becoming clogged and being unable to adequately vent the cavity.

FIGS. 2A-4 illustrate a second embodiment of a pouch 110 according to the present invention.

Where the features of pouch 110 are equivalent to those of pouch 10, like reference numerals have been used. Equivalent features are configured in the same way in pouch 110 as pouch 10 described herein, unless otherwise stated herein. For features that are common, reference should be made to the preceding description also.

Pouch 110 is formed of an inner wall 118b and an outer wall 120b sealed about their periphery and define a cavity for containing a stomal output. Again, the cavity includes a first section 112, a second section 114 and a third section 116 which are generally rounded in shape with convex curved edges, defining an upper section 112, lower section 116 and intermediate section 114 positioned between the upper and lower sections 112, 116. The upper, intermediate and lower sections 112, 114, 116 are separated by waisted sections 113, 115 which are narrower in width than upper, intermediate and lower sections 112, 114, 116. Specifically, the pouch 110 includes a first waisted section 113 which is located between the upper section 112 and intermediate section 114, with the maximum width of the upper section 112 and intermediate section 114 being greater than the minimum width of the first waisted section 113. Further, the pouch 110 includes a second waisted section 115 which is located between the intermediate section 114 and lower section 116, with the maximum width of the intermediate section 114 and lower section 116 being greater than the minimum width of the second waisted section 115.

As with pouch 10, the inner and outer walls 118b, 120b are formed of a flexible, plastics sheet material and are provided with inner and outer comfort layers 118a, 120a formed of woven, fabric material and which overlie respective inner and outer walls 118b, 120b. Again, a stomal inlet 148 is provided in the upper section 112 of the pouch 110 for receiving stomal output into the cavity, with an ostomy wafer 124 located within an aperture 146 in the inner comfort layer 118a and positioned over the stomal inlet 148, in use. The ostomy wafer 124 is configured in the same way as ostomy wafer 24 described hereinabove. The pouch similarly includes a separation filter 150 and filter arrangement 130 configured in substantially the same manner as separation filter 50 and filter arrangement 30 of pouch 10.

Pouch 110 differs in that it is an "open" pouch 110 which includes a drain 132 for draining stomal output from the cavity.

The drain 132 is formed in the lower section 116 of the pouch 110, and comprises a drain aperture 135 comprising an unsealed portion of the periphery of the pouch 110, i.e. a region of the periphery of the inner and outer walls 118b, 120b which is not sealed together. Stomal output may be released from the cavity through the drain aperture 135, in use.

In the illustrated embodiment, the drain 132 is integral with the inner and outer walls 118b, 120b, and forms an elongated portion of the pouch 110 which extends downwardly from a lower edge of the lower section 116. The inner and outer comfort layers 118a, 120a are not provided over the drain 132. Similarly, the separation filter 150 aligns with the inner and outer comfort layers 118a, 120a does not extend into the drain 132. The separation filter 150 here is not sealed to the inner and outer walls 118b, 120b at its lowermost edge, allowing for stomal output to drain from both the first and second chambers of the cavity through the drain 132.

Figure 3B:
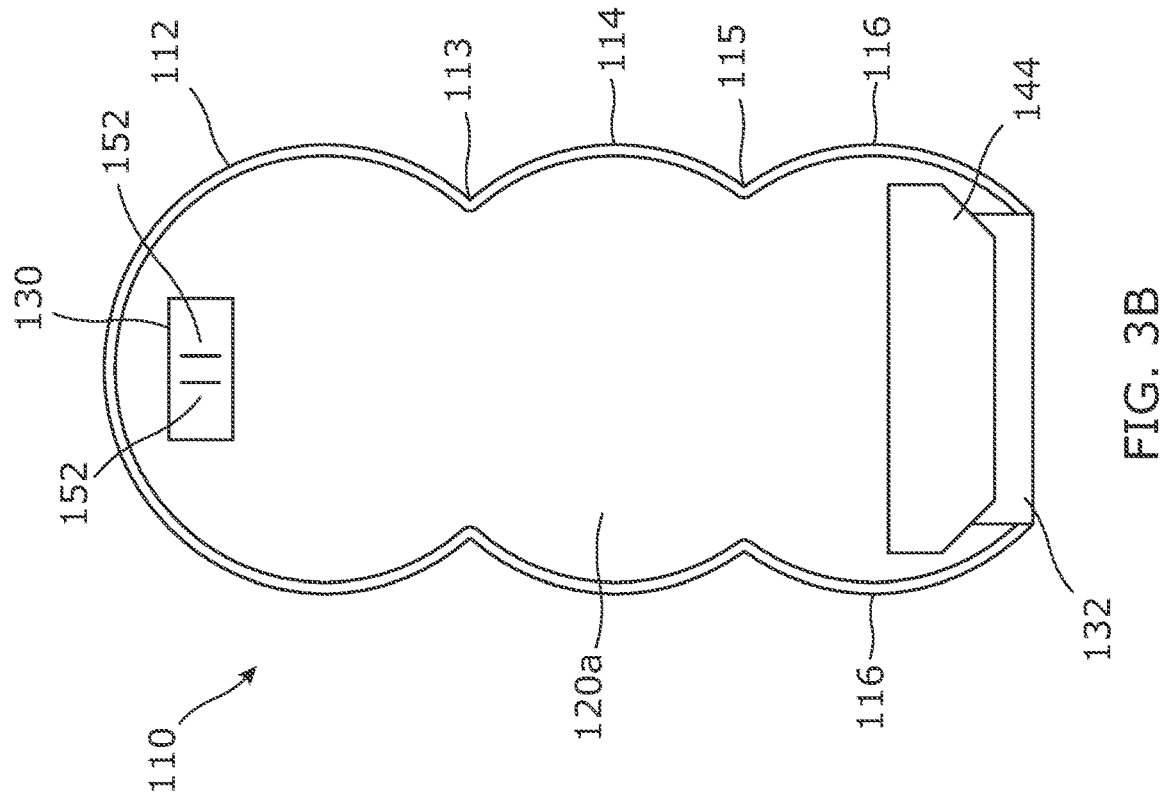
FIG. 3B is a further side perspective view of the ostomy pouch shown in FIGS. 2A, 2B and 3A.
Figure 3A:
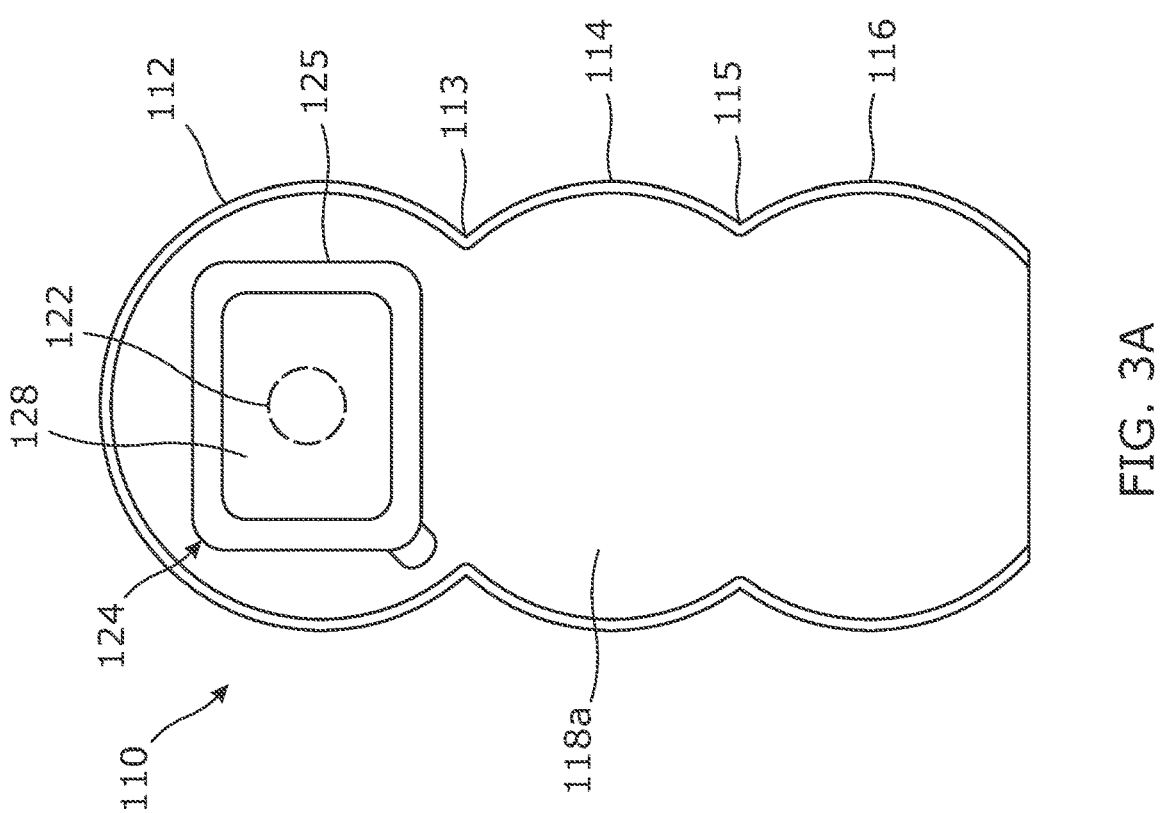
FIG. 3A is a further side perspective view of the ostomy pouch shown in FIGS. 2A and 2B.
Figure 4:
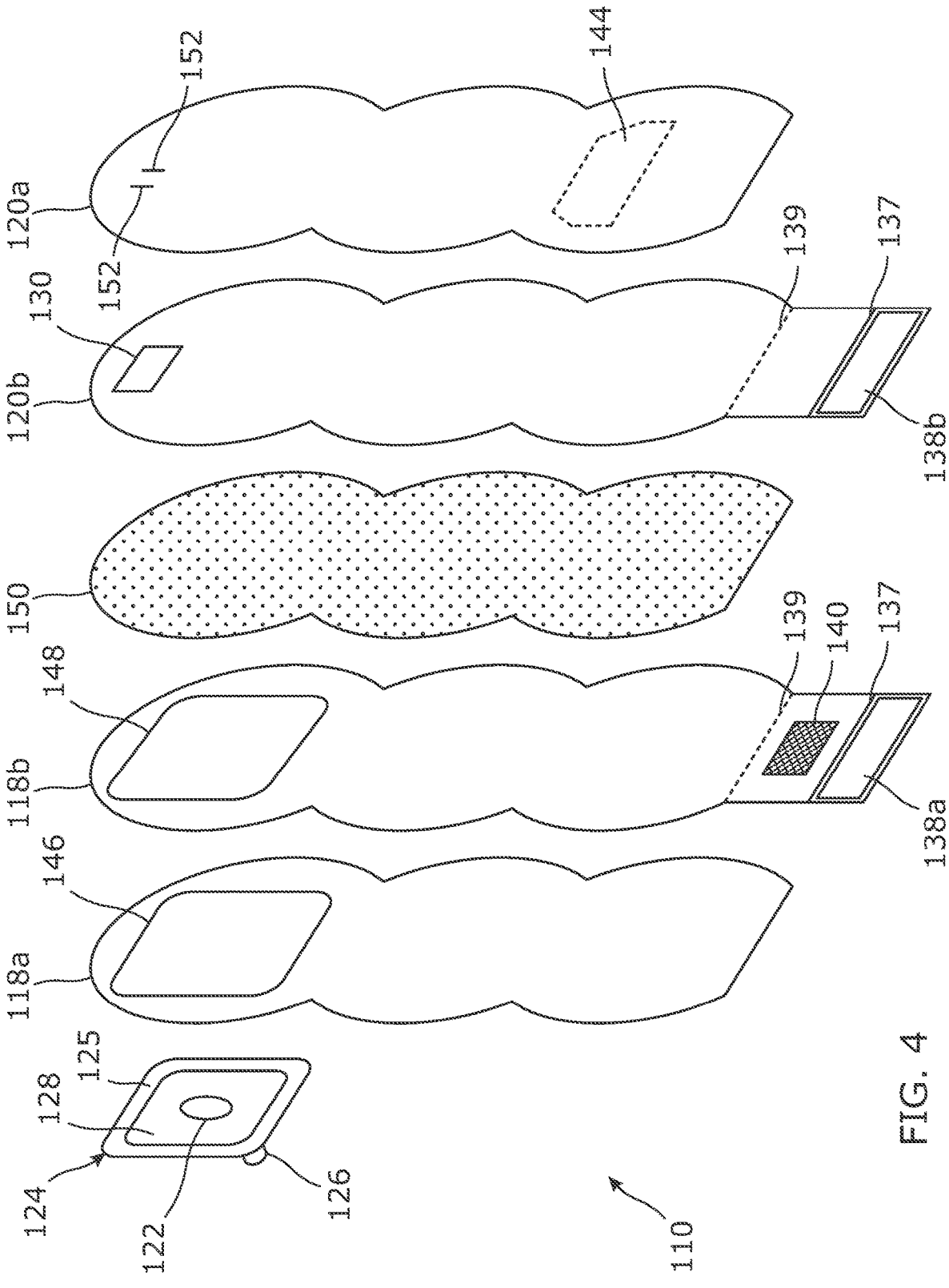
FIG. 4 is an exploded perspective view of the ostomy pouch shown in FIGS. 2A-3B.

In the illustrated embodiment, the drain 132 is a deployable drain 132 which is moveable between a deployed position (shown in FIGS. 2A and 2B) to a stowed position (shown in FIGS. 3A and 3B). Moving the drain 132 to the stowed position effectively closes off the drain aperture 135 preventing release of stomal output from the cavity. Specifically, the drain 132 is foldable between the deployed and stowed positions roughly about fold lines 137, 139 in the drain 132. The fold lines define the drain 132 into first and second segments 134, 136, with the segments 134, 136 being foldable on top of one another, e.g. about fold lines 137, 139 when moving from the deployed position to the stowed position.

Pursing strips 138*a*, 138*b* are provided on opposing sides of the first segment 134 of the drain 132, specifically on the portions of the inner and outer walls 118*b*, 120*b* defining the first segment 134 of the drain 132, and provide localised rigidity to the drain 132 and assist with the opening of the drain aperture 135, in use. Specifically, the pursing strips 138*a*, 138*b* may be squeezed laterally to arch the pursing strips 138*a*, 138*b* (and the inner and outer walls 118*b*, 120*b* respectively) in opposing directions to open the drain aperture 135.

The drain 132 includes a first fastening element in the form of a strip of hook fasteners 140 provided on an outer surface of the inner wall 118*b*. Specifically, the strip of hook fasteners 140 is provided on the outer surface of the portion of the inner wall 118*b* defining the second segment 136 of the drain 132. A corresponding second fastening element 142 is provided on a flap 144 attached (e.g. adhesively secured) to an outer surface of the outer comfort layer 120*a*. The second fastening element similarly takes the form of a strip of hook fasteners 142.

In use, the drain 132 is moved from the deployed position to the stowed position by folding the drain 132 about fold lines 137, 139 upwards and away from the ostomate, by first bringing the first segment 134 adjacent to and overlying the second segment by folding along fold line 137, and subsequently folding the second segment 136 about the fold line 139 bringing the folded drain 132 adjacent to and overlying a portion of the outer comfort layer 120*a* as shown in FIG. 3B. The flap 144 may then be folded downwards bringing the second fastening element 142 into contact and engagement with the first fastening element 140 to retain the drain 132 in the stowed position. The drain 132 is moved from the stowed position to the deployed position in the opposite manner.

Figure 5:
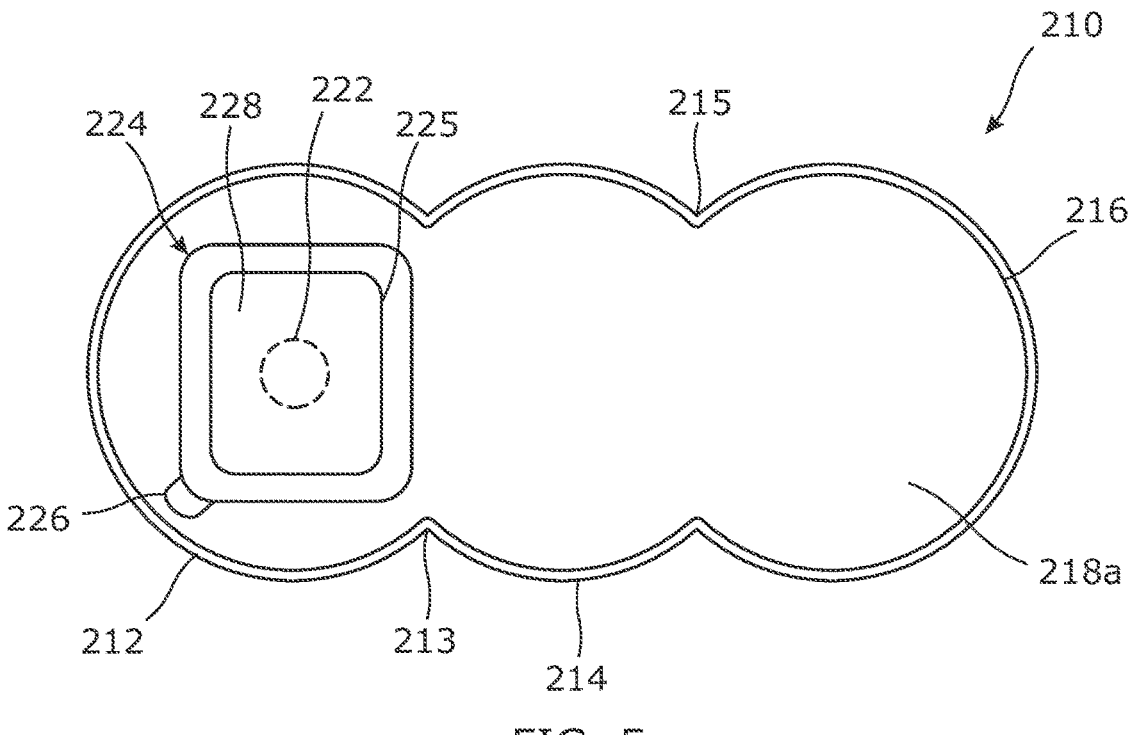
FIG. 5 is a side perspective view of a third embodiment of an ostomy pouch of the invention.

FIG. 5 illustrates a third embodiment of a pouch 210 according to the present invention. Where the features of pouch 210 are equivalent to those of pouches 10, 110 like reference numerals have been used. Equivalent features are configured in the same way in pouch 210 as pouches 10, 110 described herein, unless otherwise stated herein. For features that are common, reference should be made to the preceding description also.

Pouch 210 differs in that it is configured for use in a horizontal orientation. Here, the inner outer walls are sealed about their periphery and define a closed cavity which is split into a left-side section 212, right side section 216 and intermediate section 214, separated by waisted sections 213, 215 which are narrower in width than left side, intermediate and right side sections 212, 214, 216. The pouch 210 is otherwise configured in the same manner as pouch 10 discussed herein with the left side section 212 specifically configured in the same manner as upper section 12.

Figure 6:
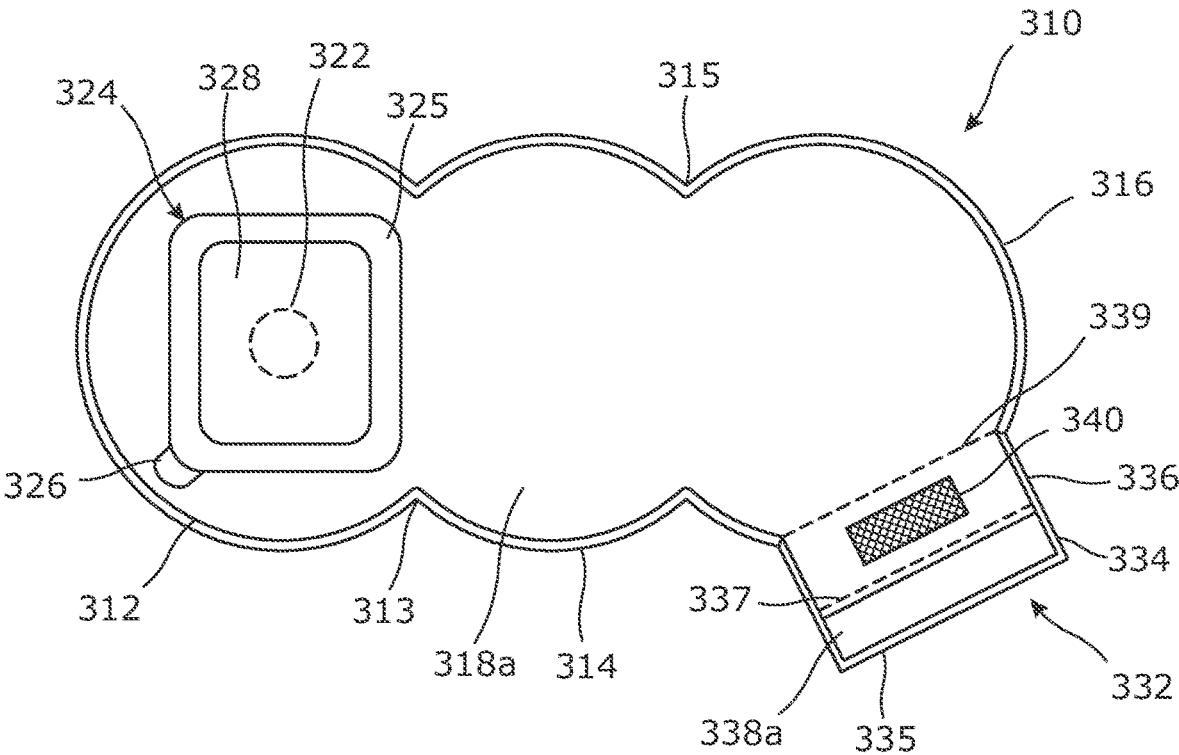
FIG. 6 is a side perspective view of a fourth embodiment of an ostomy pouch of the invention.

FIG. 6 illustrates a fourth embodiment of a pouch 310 in accordance with the invention. Where the features of pouch 310 are equivalent to those of pouches 10, 110, 210, like reference numerals have been used. Equivalent features are configured in the same way in pouch 310 as pouches 10, 110, 210 described herein, unless otherwise stated herein. For features that are common, reference should be made to the preceding description also.

Pouch 310 is also configured for use in a horizontal orientation. Here, the inner outer walls are sealed about their periphery and define an open cavity which is split into a left-side section 312, right side section 316 and intermediate section 314, separated by waisted sections 313, 315 which are narrower in width than left side, intermediate and right side sections 312, 314, 316. The pouch 310 is otherwise configured in the same manner as pouch 110 discussed herein with the left side section 312 specifically configured in the same manner as upper section 112, and the right side section 316 configured in substantially the same manner as lower section 216, with a drain 332 provided in a lowermost edge thereof.

The one or more embodiments are described above by way of example only. Many variations are possible without departing from the scope of protection afforded by the appended claims.

The invention claimed is:

1. An ostomy pouch, comprising:
an inner wall and an outer wall sealed about at least part of a periphery of the inner wall and the outer wall to define a cavity for containing a stomal output, the cavity including, at least
a first section, a second section and a third section each comprising a generally rounded shape and at least one continuously curved edge,
a first waisted section located between the first section and second section, and
a second waisted section located between the second section and the third section,
wherein the first and second sections have a maximum width greater than a minimum width of the first waisted section
wherein the second and third sections have a maximum width greater than a minimum width of the second waisted section, and
wherein one or more radii of curvatures for the at least one continuously curved edge of the second section are greater than one or more radii of curvature of the at least one continuously curved edge of each of the first and/or third sections.

2. An ostomy pouch as claimed in claim 1, wherein the pouch is configured to be used in a substantially vertical orientation, with the first section forming an upper section of the pouch, the third section forming a lower section of the pouch, and the second section forming an intermediate section between the upper and lower sections.

3. An ostomy pouch as claimed in claim 1, wherein the pouch is configured to be used in a substantially horizontal orientation, with the first section forming a first end section, the third section forming a second end section and the second section forming an intermediate section between the first and second end sections.

4. An ostomy pouch as claimed in claim 3, wherein the first section forms a right-side section of the pouch and the third section forms a left-side section of the pouch.

5. An ostomy pouch as claimed in claim 1, wherein the inner wall of the pouch comprises an inlet for receiving the stomal output into the cavity.

6. An ostomy pouch as claimed in claim 5, wherein the inlet is provided within a portion of the inner wall defining at least part of the first section of the cavity.

7. An ostomy pouch as claimed in claim 5, wherein the inlet is provided within a portion of the inner wall defining at least part of the second section of the pouch.

8. An ostomy pouch as claimed in claim 1, comprising an open pouch which includes a drain for releasing stomal output from the cavity, the drain comprising a drain aperture comprising an opening within the pouch for releasing stomal output from the cavity.

9. An ostomy pouch as claimed in claim 8, wherein the drain comprises a deployable drain, which is moveable between a stowed position and a deployed position.

10. An ostomy pouch as claimed in claim 9, wherein the drain is provided in the third section of the pouch.

11. An ostomy pouch as claimed in claim 1, comprising a filter arrangement which includes a vent for venting of gaseous stomal output from the cavity, and an odour filter.

12. An ostomy pouch as claimed in claim 11, wherein the filter arrangement comprises a pre-filter configured to control the content of stomal output in contact with the vent and/or odour filter.

13. An ostomy pouch as claimed in claim 11, wherein the filter arrangement is provided within, or is associated with the first section of the pouch.

14. An ostomy pouch as claimed in claim 1, wherein the maximum widths of the first, second and/or third sections are substantially equal.

15. An ostomy pouch as claimed in claim 1, wherein the maximum widths of the first, second and/or third sections are different.

16. An ostomy pouch as claimed in claim 15, wherein the maximum width of the first section is greater than the maximum width of the second section, and the maximum width of the second section is greater than the maximum width of the third section.

17. An ostomy pouch of claim 1, wherein opposing edges of the first and/or second waisted sections are each be concavely-curved.

18. An ostomy pouch of claim 1, wherein the at least one continuously curved edge of the first, second and/or third sections is convexly curved.

19. An ostomy pouch of claim 1, wherein the cavity is sub-divided into two or more chambers; the ostomy pouch comprising a separation wall between the inner and outer walls dividing the cavity into first and second chambers, and wherein the separation wall comprises a fluid-permeable filtering element operable to filter fluid stomal output from solid stomal output.

20. An ostomy pouch of claim 1, further comprising a wafer aperture and ostomy wafer 24 disposed therein in the first section of the pouch, wherein the ostomy wafer comprises a moldable adhesive configured to be manipulated to adjust the shape and size of a central aperture under application of rolling force by a user.

21. An ostomy pouch of claim 11, further comprising a removable filter cover label configured to be positioned over the filter vent in use to conceal openings therein and prevent ingress of water therethrough during use.

\* \* \* \* \*